(12) United States Patent
Tsuzaka et al.

(10) Patent No.: US 9,718,977 B2
(45) Date of Patent: Aug. 1, 2017

(54) WATER-BASED INK FOR INK-JET RECORDING AND METHOD FOR EVALUATING WATER-BASED INK FOR INK-JET RECORDING

(71) Applicant: Brother Kogyo Kabushiki Kaisha, Nagoya-shi, Aichi-ken (JP)

(72) Inventors: Yuka Tsuzaka, Nagoya (JP); Mitsunori Maeda, Nagoya (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 0 days.

(21) Appl. No.: 14/867,651

(22) Filed: Sep. 28, 2015

(65) Prior Publication Data

US 2016/0289474 A1 Oct. 6, 2016

(30) Foreign Application Priority Data

Mar. 31, 2015 (JP) .................................. 2015-073800

(51) Int. Cl.
| | | |
|---|---|---|
| *C09D 11/30* | (2014.01) | |
| *C09D 11/322* | (2014.01) | |
| *C09D 11/324* | (2014.01) | |
| *C09D 11/00* | (2014.01) | |
| *C09D 11/38* | (2014.01) | |
| *G01N 1/40* | (2006.01) | |
| *G01N 21/59* | (2006.01) | |

(52) U.S. Cl.
CPC ............ *C09D 11/324* (2013.01); *C09D 11/00* (2013.01); *C09D 11/30* (2013.01); *C09D 11/322* (2013.01); *C09D 11/38* (2013.01); *G01N 1/4022* (2013.01); *G01N 21/59* (2013.01); *G01N 2001/4027* (2013.01)

(58) Field of Classification Search
CPC ............................... C09D 11/30; C09D 11/322
See application file for complete search history.

(56) References Cited

U.S. PATENT DOCUMENTS

| | | |
|---|---|---|
| 5,609,671 A | 3/1997 | Nagasawa |
| 5,837,045 A | 11/1998 | Johnson et al. |
| 7,819,962 B2 | 10/2010 | Gu |
| 7,922,805 B2 | 4/2011 | Kowalski et al. |
| 8,016,404 B2 | 9/2011 | Kato et al. |
| 2006/0197814 A1* | 9/2006 | Doi ........................ C09D 11/30 347/100 |
| 2006/0201380 A1 | 9/2006 | Kowalski et al. |

(Continued)

FOREIGN PATENT DOCUMENTS

| | | |
|---|---|---|
| JP | H0803498 A | 1/1996 |
| JP | 2000-513396 A | 10/2000 |

(Continued)

OTHER PUBLICATIONS

Jun. 28, 2016—(EP) Extended Search Report—App 15187200.9.

*Primary Examiner* — Veronica F Faison
(74) *Attorney, Agent, or Firm* — Banner & Witcoff, Ltd.

(57) ABSTRACT

There is provided a water-based ink for ink jet-recording containing a pigment; a surfactant; and water, wherein a slope value of the water-based ink at an evaporation rate of 0% is not more than 15%/hour; and a slope value of the water-based ink at an evaporation rate of 30% is not less than 9%/hour, the slope value of the water-based ink being measured by a centrifugal transmission sedimentation method.

13 Claims, 1 Drawing Sheet

(56) References Cited

U.S. PATENT DOCUMENTS

| | | |
|---|---|---|
| 2006/0256175 A1 | 11/2006 | Kanaya |
| 2007/0100023 A1 | 5/2007 | Burns et al. |
| 2007/0100024 A1 | 5/2007 | Gu et al. |
| 2008/0241398 A1 | 10/2008 | Kato et al. |
| 2009/0229489 A1 | 9/2009 | Gu |
| 2010/0186625 A1 | 7/2010 | Kanaya |
| 2011/0048278 A1* | 3/2011 | Kiyomoto ............ C09D 11/322 106/31.86 |
| 2012/0081477 A1 | 4/2012 | Nagano |
| 2014/0292901 A1 | 10/2014 | Ohishi |

FOREIGN PATENT DOCUMENTS

| | | |
|---|---|---|
| JP | 2004-231711 A | 8/2004 |
| JP | 2005-232302 A | 9/2005 |
| JP | 2006-274031 A | 10/2006 |
| JP | 2006-274301 A | 10/2006 |
| JP | 2008-524400 A | 7/2008 |
| JP | 2008-246821 A | 10/2008 |
| JP | 2009-515007 A | 4/2009 |
| JP | 2011-515535 A | 5/2011 |

\* cited by examiner

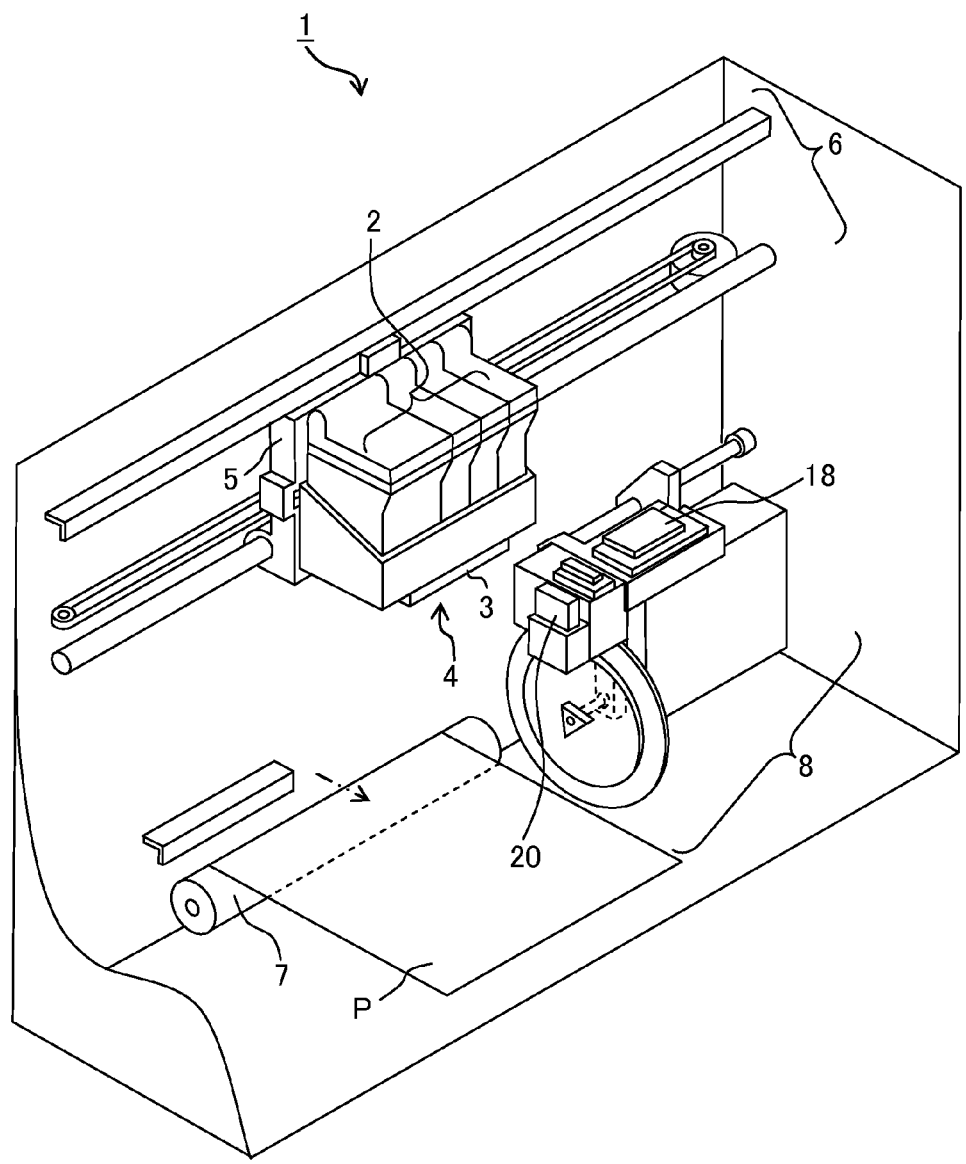

WATER-BASED INK FOR INK-JET RECORDING AND METHOD FOR EVALUATING WATER-BASED INK FOR INK-JET RECORDING

CROSS REFERENCE TO RELATED APPLICATION

The present application claims priority from Japanese Patent Application No. 2015-073800, filed on Mar. 31, 2015, the disclosure of which is incorporated herein by reference in its entirety.

BACKGROUND OF THE INVENTION

Field of the Invention

The present invention relates to a water-based ink for ink-jet recording, an ink cartridge, an ink-jet recording apparatus, an ink-jet recording method and a method for evaluating water-based ink for ink-jet recording.

Description of the Related Art

As an ink usable for ink-jet recording, there is proposed a water-based pigment ink containing a pigment and water (see, for example, Japanese Patent Application Laid-open No. 2004-231711).

Regarding the above-described water-based pigment ink, when an attempt is made to improve the storing stability, the optical density (OD value) is lowered in some cases. In view of this situation, an object of the present teaching is to provide a water-based pigment ink for ink-jet recording capable of realizing both of high optical density (OD value) and high storing stability.

SUMMARY OF THE INVENTION

According to a first aspect of the present teaching, there is provided a water-based ink for ink-jet recording including: a pigment; a surfactant; and water, wherein a slope value of the water-based ink at an evaporation rate of 0% is not more than 15%/hour; and a slope value of the water-based ink at an evaporation rate of 30% is not less than 9%/hour, the slope value of the water-based ink being measured by a centrifugal transmission sedimentation method.

According to a second aspect of the present teaching, there is provided a method for evaluating a water-based ink for ink-jet recording containing a pigment, a surfactant and water, the method including: performing a first evaluation of aggregation for measuring a slope value of the water-based ink at an evaporation rate of 0%, by a centrifugal transmittance sedimentation method; and performing a second evaluation of aggregation for measuring a slope value of the water-based ink at an evaporation rate of 30%, by the centrifugal transmittance sedimentation method.

BRIEF DESCRIPTION OF THE DRAWINGS

FIGURE is a schematic perspective view depicting an example of the configuration of an ink-jet recording apparatus of the present teaching.

DESCRIPTION OF THE PREFERRED EMBODIMENTS

An explanation will be given about a water-based ink for ink-jet recording of the present teaching. In the following, the water-based ink for ink-jet recording is also referred as "water-based ink" or "ink" in some cases. The water-based ink for ink-jet recording of the present teaching includes a pigment, a surfactant, and water.

The pigment is not particularly limited, and is exemplified, for example, by a carbon black, an inorganic pigment, an organic pigment, etc. The carbon black is not particularly limited, and is exemplified, for example, by furnace black, lamp black, acetylene black, channel black, etc. The inorganic pigment includes, for example, titanium oxide, inorganic pigments based on iron oxide, inorganic pigments based on carbon black, etc. The organic pigment includes, for example, azo-pigments such as azo lake, insoluble azo-pigment, condensed azo-pigment, chelate azo-pigment, etc.; polycyclic pigments such as phthalocyanine pigment, perylene and perynon pigments, anthraquinone pigment, quinacridone pigment, dioxadine pigment, thioindigo pigment, isoindolinone pigment, quinophthalone pigment etc.; dye lake pigments such as basic dye type lake pigment, acid dye type lake pigment etc.; nitro pigments; nitroso pigments; aniline black daylight fluorescent pigment; and the like. Any other pigment is also usable provided that the pigment is dispersible in a water phase (aqueous phase). Specific example of the pigments as described above include, for example, C. I. Pigment Blacks 1, 6, and 7; C. I. Pigment Yellows 1, 2, 3, 12, 13, 14, 15, 16, 17, 55, 73, 74, 75, 78, 83, 93, 94, 95, 97, 98, 114, 128, 129, 138, 150, 151, 154, 180, 185, and 194; C. I. Pigment Oranges 31 and 43; C. I. Pigment Reds 2, 3, 5, 6, 7, 12, 15, 16, 48, 48:1, 53:1, 57, 57:1, 112, 122, 123, 139, 144, 146, 149, 150, 166, 168, 175, 176, 177, 178, 184, 185, 190, 202, 221, 222, 224, and 238; C. I. Pigment Violet 19 and 196; C. I. Pigment Blues 1, 2, 3, 15, 15:1, 15:2, 15:3, 15:4, 16, 22, and 60; C. I. Pigment Greens 7 and 36; solid solutions of the above-listed pigments; and the like. In the water-based ink of the present teaching, the pigment may be dispersed in water by a dispersant. As the dispersant, it is allowable to use, for example, any general polymeric dispersant, etc. Alternatively, in the water-based ink of the present teaching, the pigment may be subjected to polymer capsulation.

The pigment may be a self-dispersible pigment. The self-dispersible pigment is dispersible in water without using any dispersant, for example, owing to the fact that at least one of the hydrophilic functional group and the salt thereof including, for example, carbonyl group, hydroxyl group, carboxylic acid group, sulfonic acid group (sulfonate group), phosphoric acid group (phosphate group), etc. is introduced into the surfaces of the particles of pigment by the chemical bond directly or with any group intervening therebetween. It is possible to use self-dispersible pigments subjected to the treatment by any one of methods described, for example, in Japanese Patent Application Laid-open No. HEIS-3498 corresponding to U.S. Pat. No. 5,609,671, Published Japanese Translation of PCT International Publication for Patent Application No. 2000-513396 corresponding to U.S. Pat. No. 5,837,045, Published Japanese Translation of PCT International Publication for Patent Application No. 2008-524400 corresponding to United States Patent Application Publication No. US 2006/0201380, Published Japanese Translation of PCT International Publication for Patent Application No. 2009-515007 corresponding to United States Patent Application Publications No. US 2007/0100023 and No. US 2007/0100024, Published Japanese Translation of PCT International Publication for Patent Application No. 2011-515535 corresponding to United States Patent Application Publications No. US 2009/0229489, etc. An inorganic pigment and an organic pigment may each be used as a material of the self-dispersible pigment. Further, a pigment which is suitable for the above-described treatment includes, for example, carbon black such as "MA8", "MA100" and "#2650" produced by Mitsubishi Chemical Corporation, etc. As the self-dispersible pigment, it is possible, for example, to use a commercially available product. The commercially available product includes, for example, "CAB-O-JET (trade name) 200", "CAB-O-JET (trade name) 250C", "CAB-O-JET (trade name) 260M", "CAB-O-JET (trade name) 270Y", "CAB-O-JET (trade name) 300", "CAB-O-JET (trade name) 400", "CAB-O-JET (trade name) 450C", "CAB-O-JET (trade name) 465M" and "CAB-O-JET (trade name) 470Y" produced by Cabot Specialty Chemicals; "BONJET (trade name) BLACK CW-2" and "BONJET (trade name) BLACK CW-3" produced by Orient Chemical Industries, Ltd.; "LIO-JET (trade name) WD BLACK 002C" produced by Toyo Ink Mfg. Co., Ltd.; and the like.

The solid content blending amount of the pigment in the entire amount of the water-based ink (hereinafter referred to as a "blending amount of the pigment" or "pigment blending amount" in some cases) is, for example, not less than 0.1% by weight, preferably not less than 1% by weight, and more preferably not less than 4% by weight. In a case that the solid content blending amount of pigment is made to be not less than 4% by weight, a water-based ink having a higher optical density (OD value) can be obtained. The solid content blending amount of pigment is further preferably not less than 6% by weight, is further more preferably not less than 8% by weight. Although the upper limit value of the solid content blending amount is not particularly limited, the upper limit value is, for example, not more than 20% by weight, preferably not more than 15% by weight, and more preferably not more than 10% by weight.

The average particle size of the pigment is, for example, in a range of 60 nm to 200 nm, preferably in a range of 100 nm to 180 nm, and more preferably in a range of 140 nm to 160 nm. By making the average particle size in the range of 140 nm to 160 nm, a water-based ink having a higher optical density (OD value) can be obtained. The average particle size can be calculated, for example, by diluting the pigment so that the solid content blending amount is 0.02% by weight and then by using a dynamic light scattering particle size distribution measuring apparatus LB-550 manufactured by HORIBA, Ltd. so as to obtain the intensity of scattered light as the reference for the average particle size.

From viewpoint of improving the optical density (OD value), the pigment is preferably a carbon black of which average particle size is in a range of 140 nm to 160 nm, is more preferably a self-dispersible carbon black, and is further more preferably a self-dispersible carbon black modified by a carboxyl group. The water-based ink may contain another colorant such as a dye, etc., in addition to the carbon black; alternatively, it is allowable that the water-based ink contains no other colorant different from the carbon black.

The surfactant is not particularly limited, and is exemplified, for example, by nonionic surfactants of "OLFIN (trade name)" series produced by Nisshin Chemical Co., Ltd.; nonionic surfactants of "EMULGEN (trade name)" series, "RHEODOL (trade name)" series, "EMASOL (trade name)" series, "EXCEL (trade name)" series, "EMANON (trade name)" series, "AMIET (trade name)" series, "AMINON (trade name)" series, etc., produced by KAO Corporation; nonionic surfactants of "SORBON (trade name)" series produced by Toho Chemical Industry Co., Ltd.; nonionic surfactants of "DOBANOX (trade name)" series, "LEOCOL (trade name)" series, "LEOX (trade name)" series, "LAOL, LEOCON (trade name)" series, "LIONOL (trade name)" series, "CADENAX (trade name)" series, "LIONON (trade name)" series, "LEOFAT (trade name)" series, etc., produced by Lion Corporation; anionic surfactants of "EMAL (trade name)" series, "LATEMUL (trade name)" series, "VENOL (trade name)" series, "NEOPELEX (trade name)" series, NS SOAP, KS SOAP, OS SOAP, and "PELEX (trade name)" series, etc., produced by Kao Corporation; anionic surfactants of "LIPOLAN (trade name)" series, "LIPON (trade name)" series, "SUNNOL (trade name)" series, "LIPOTAC (trade name)" series, "TE, ENAGICOL (trade name)" series, "LIPAL (trade name)" series, and "LOTAT (trade name)" series, etc., produced by Lion Corporation; cationic surfactants "KACHIOGEN (trade name) ES-OW" and "KACHIOGEN (trade name) ES-L" produced by Dai-Ichi Kogyo Seiyaku Co., Ltd., etc. It is allowable that only one kind of the surfactant is used singly, or that two or more kinds of the surfactant are used in a mixed manner. The blending amount of the surfactant in the entire amount of the water-based ink is, for example, in a range of 0.1% by weight to 10% by weight, preferably in a range of 0.1% by weight to 8% by weight, and more preferably in a range of 0.1% by weight to 5% by weight.

In the water-based ink, it is preferable that the surfactant includes a nonionic surfactant, and the HLB (Hydrophile-Lipophile Balance) of the nonionic surfactant is in a range of 8 to 12. The nonionic surfactant of which HLB is in a range of 8 to 12 is preferably a nonionic surfactant having an ethylene oxide group, more preferably an acetylenic glycol-based nonionic surfactant represented by the following formula (1). Among the nonionic surfactants, the acetylenic glycol-based nonionic surfactant represented by the following formula (1) particularly has a strong property to spread laterally (horizontally) on a recording medium, thereby making it possible to obtain a water-based ink having a higher optical density (OD value).

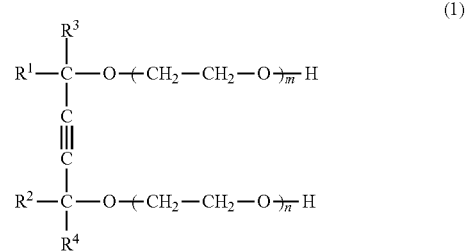

In the formula (1), "m" and "n" may be identical to each other or different from each other, and are numbers satisfying: $m+n=1$ to 15, preferably satisfying: $m+n=3$ to 11, and more preferably satisfying: $m+n=1$ to 6; $R^1$, $R^2$, $R^3$ and $R^4$ may be identical to one another or different from one another, and each of $R^1$, $R^2$, $R^3$ and $R^4$ is a straight-chain or branched-chain alkyl group of which carbon atom number is 1 to 5. $R^1$, $R^2$, $R^3$ and $R^4$ are exemplified, for example, by methyl group, ethyl group, propyl group, isopropyl group, butyl group and isobutyl group. Each of $R^1$, $R^2$, $R^3$ and $R^4$ is preferably methyl group or isopropyl group.

The acetylenic glycol-based nonionic surfactant represented by the formula (1), for example, by "OLFIN (trade name) E1004" ($m+n=4$), "OLFIN (trade name) E1010" ($m+n=10$) which are produced by Nisshin Chemical Co., Ltd.; and the like.

The blending amount of the nonionic surfactant in the entire amount of the water-based ink (nonionic surfactant ratio) is, for example, in a range of 0.01% by weight to 10% by weight and preferably in a range of 0.05% by weight to 5% by weight. In a case that the water-based ink contains the nonionic surfactant having such a property that the nonionic surfactant spreads laterally (horizontally) on a recording medium by an amount of not less than 0.05% by weight, it is possible to obtain a water-based ink having a higher optical density (OD value). On the other hand, the nonionic surfactant tends to have a low solubility to water in some case, and in a case that the water-based ink contains a large amount of the nonionic surfactant, there is such a fear that the storing stability of the water-based ink might be lowered. Accordingly, in a case that the blending amount of the nonionic surfactant in the water-based ink is made to be not more than 5% by weight, it is possible to obtain a water-based ink having a high storing stability. The nonionic surfactant ratio is more preferably in a range of 0.1% by weight to 2% by weight, further more preferably in a range of 0.1% by weight to 0.5% by weight, particularly preferably in a range of 0.2% by weight to 0.5% by weight. In a case that the average particle size of the carbon black is made to be in the range of 140 nm to 160 nm and the nonionic surfactant ratio is made to be in the range of 0.1% by weight to 0.5% by weight, it is possible to obtain a water-based ink excellent in the storing stability. Further, in a case that the average particle size of the carbon black is made to be in the range of 140 nm to 160 nm and the nonionic surfactant ratio is made to be in the range of 0.2% by weight to 0.5% by weight, it is possible to obtain a water-based having a higher optical density (OD value).

Further, a weight ratio (N/P) of a blending amount (N) of the acetylenic glycol-based nonionic surfactant represented by the formula (1) to a blending amount (P) of the pigment in the water-based ink is, for example, in a range of (N/P)=0.1/100 to 20/100, preferably in a range of (N/P)=0.5/100 to 10/100, and more preferably in a range of (N/P)=1.2/100 to 8.4/100. By making the weight ratio (N/P) in the above range, it is possible to further improve the optical density (OD value) and the storing stability of the water-based ink.

Furthermore, in a case that the water-based ink contains the acetylenic glycol-based nonionic surfactant represented by the formula (1), the water-based ink preferably further contains an anionic surfactant. The acetylenic glycol-based nonionic surfactant represented by the formula (1) has a low solubility to water. The anionic surfactant assists the nonionic surfactant to dissolve into the water, thereby improving the storing stability of the water-based ink. The blending amount of the anionic surfactant in the water-based ink is, for example, in a range of 0.01% by weight to 5% by weight, preferably in a range of 0.02% by weight to 1% by weight, and more preferably in a range of 0.08% by weight to 0.42% by weight. Further, a weight ratio (A/N) of a blending amount (A) of the anionic surfactant to the blending amount (N) of the acetylenic glycol-based nonionic surfactant represented by the formula (1) in the water-based ink is, for example, in a range of (A/N)=0.1 to 2.0, preferably in a range of (A/N)=0.2 to 1.0, and more preferably in a range of (A/N)=0.2 to 0.8.

The surfactant contained in the water-based ink may be composed only of the acetylenic glycol-based nonionic surfactant represented by the formula (1) and the anionic surfactant. Namely, it is allowable that the surfactant does not contain any nonionic surfactant different from the acetylenic glycol-based nonionic surfactant represented by the formula (1) or any cationic surfactant. By making the water-based ink to contain, as the surfactant, only the acetylenic glycol-based nonionic surfactant represented by the formula (1) and the anionic surfactant, it is easy to realize both the improved (high) optical density (OD value) and the high storing stability.

The water is preferably ion-exchanged water or pure water (purified water). The blending amount of the water (water ratio) in the entire amount of the water-based ink may be, for example, in a range of 30% by weight to 90% by weight, and preferably in a range of 40% by weight to 80% by weight. The blending amount of the water in the entire amount of the water-based ink may be, for example, the balance of the other components.

The water-based ink of the present teaching may further contain a water-soluble organic solvent. The water-soluble organic solvent is exemplified, for example, by a humectant which prevents the water-based ink from drying at an end of a nozzle in an ink-jet head, a penetrant which adjusts the drying velocity on a recording medium, etc.

The humectant is not particularly limited, and is exemplified, for example, by lower alcohols such as methyl alcohol, ethyl alcohol, n-propyl alcohol, isopropyl alcohol, n-butyl alcohol, sec-butyl alcohol, and tert-butyl alcohol; amides such as dimethylformamide and dimethylacetamide; ketones such as acetone; ketoalcohols (ketone alcohols) such as diacetone alcohol; ethers such as tetrahydrofuran and dioxane; polyethers such as polyalkylene glycol; polyvalent alcohols such as alkylene glycol, glycerol, trimethylolpropane, and trimethylolethane; 2-pyrrolidone; N-methyl-2-pyrrolidone; 1,3-dimethyl-2-imidazolidinone; and the like. The polyalkylene glycol is exemplified, for example, by polyethylene glycol, polypropylene glycol, etc. The alkylene glycol is exemplified, for example, by ethylene glycol, propylene glycol, butylene glycol, diethylene glycol, triethylene glycol, dipropylene glycol, tripropylene glycol, thiodiglycol, hexylene glycol, etc. It is allowable that only one kind of the humectant as described above is used singly, or two or more kinds of the humectant are used in combination. Among the above-described humectants, it is preferable to use polyvalent alcohols such as alkylene glycol, glycerol, etc.

The blending amount of the humectant in the entire amount of the water-based ink is, for example, in a range of 0% by weight to 95% by weight, preferably in a range of 5% by weight to 80% by weight, and more preferably in a range of 5% by weight to 50% by weight.

In a case that the water-based ink contains glycerol, a blending amount of the glycerol in the entire amount of the water-based ink is, for example, in a range of 10% by weight to 30% by weight, preferably in a range of 15% by weight to 25% by weight, and more preferably in a range of 15% by weight to 25% by weight. The blending amount of the glycerol as a non-volatile solvent greatly affects the evaporation of the water-based ink. As will be described in detail later on, about 30% by weight of the component(s) contained in the water-based ink preferably evaporates when the water-based ink lands on the recording paper during the recording, in order to realize a high optical density (OD value) for the water-based ink. By making the blending amount of the glycerol in the water-based ink to be within the above range, an amount of evaporation (evaporation amount) of the water-based ink during the recording can be easily controlled to an appropriate evaporation amount. Further, a weight ratio (G/P) of a blending amount (G) of the glycerol to the blending amount (P) of the pigment in the water-based ink is, for example, in a range of (G/P)=0.5 to 7.0, preferably in a range of (G/P)=1.0 to 5.0, and more preferably in a range of (G/P)=1.0 to 4.0. By making the weight ratio (G/P) to be within this range, it is possible to easily realize both the high optical density (OD value) and the high storing stability of the water-based ink.

The penetrant is not limited, and includes, for example, glycol ether. The glycol ether is not limited, and includes, for example, ethylene glycol methyl ether, ethylene glycol ethyl ether, ethylene glycol-n-propyl ether, diethylene glycol methyl ether, diethylene glycol ethyl ether, diethylene glycol-n-propyl ether, diethylene glycol-n-butyl ether, diethylene glycol-n-hexyl ether, triethylene glycol methyl ether, triethylene glycol ethyl ether, triethylene glycol-n-propyl ether, triethylene glycol-n-butyl ether, propylene glycol methyl ether, propylene glycol ethyl ether, propylene glycol-n-propyl ether, propylene glycol-n-butyl ether, dipropylene glycol methyl ether, dipropylene glycol ethyl ether, dipropylene glycol-n-propyl ether, dipropylene glycol-n-butyl ether, tripropylene glycol methyl ether, tripropylene glycol ethyl ether, tripropylene glycol-n-propyl ether, tripropylene glycol-n-butyl ether, etc. One kind of the penetrant may be used singly, or two or more kinds of the penetrants may be used in combination.

The blending amount of the penetrant in the entire amount of the water-based ink is, for example, in a range of 0% by weight to 20% by weight, preferably in a range of 0% by weight to 15% by weight, more preferably in a range of 1% by weight to 4% by weight.

The water-based ink may further contain a conventionally known additive, as necessary. The additive includes, for example, pH-adjusting agents, viscosity-adjusting agents, surface tension-adjusting agents, fungicides, etc. The viscosity-adjusting agents include, for example, polyvinyl alcohol, cellulose, water-soluble resin, etc.

The water-based ink can be prepared, for example, such that the pigment, the surfactant and water, and optionally other additive component(s) are mixed uniformly or homogeneously by any conventionally known method, and undissolved matters are removed by a filter or the like.

As described above, in the water-based ink, a slope value of the water-based ink at an evaporation rate of 0% evaluated (measured or obtained) by the centrifugal transmission sedimentation method is not more than 15%/hour, and a slope value of the water-based ink at an evaporation rate of 30% evaluated by the centrifugal transmission sedimentation method is not less than 9%/hour. Here, the term "water-based ink at an evaporation rate of 0%" means the water-based ink in a such state that a component (components) contained in the water-based ink has/have not evaporated yet, and the term "water-based ink at an evaporation rate of 30%" means the water-based ink in such a state that 30% by weight of a component (components) contained in the water-based ink has/have evaporated. A water-based ink in a storage state before the water-based ink is used for the recording is the "water-based ink at an evaporation rate of 0%", since any component(s) contained therein has/have not evaporated yet. On the other hand, the water-based ink discharged from the ink-jet head is presumed to be in a state close to the "water-based ink at an evaporation rate of 30%", since a solvent such as water has evaporated, and about 30% by weight of the contained component(s) has/have evaporated when the water-based ink lands on the recording medium. Namely, the term "water-based ink at an evaporation rate of 30%" presumes a water-based ink when the water-based ink lands on the recording medium during the recording (at a time the recording is performed). Further, the term "slope value" obtained by the centrifugal transmission sedimentation method means a change (increase) in the transmittance of the water-based ink per unit time when the dispersion stability of the water-based ink is evaluated by the centrifugal transmission sedimentation method. In general, as the slope value is smaller, the dispersion stability of the water-based ink is evaluated to be higher. Note that the component(s) evaporated from the water-based ink is a solvent of the water-based ink, and 70% by weight to 100% by weight of the volatile component(s) of the water-based ink is/are presumed to be water.

Since the slope values at the evaporation rate 0% and the evaporation rate 30% of the water-based ink are within the predetermined ranges, respectively, the water-based ink is capable of realizing both of the high optical density (OD value) and the high storing stability. The mechanism by which such an effect can be obtained is, for example, assumed as follows. Namely, the water-based ink in which the slope value at the evaporation rate of 0% is not more than 15%/hour has a high dispersing stability of the pigment in a storing state before any recording is performed, and thus the water-based ink has an excellent storing stability. Further, in the water-based ink in which the slope value at the evaporation rate of 30% is not less than 9%/hour, the pigment aggregates during the recording, thereby realizing a high optical density (OD value). Note that, however, the above-described mechanism is merely a presumption, and the present teaching is not limited to and restricted by this presumed mechanism.

Although the lower limit value of the slope value at the evaporation rate of 0% is not particularly limited, the lower limit is, for example, not less than 1%/hour, preferably not less than 3%/hour, more preferably not less than 5%/hour. Further, although the upper limit value of the slope value at the evaporation rate of 30% is not particularly limited, the upper limit is, for example, not more than 25%/hour, preferably not more than 20%/hour, more preferably not more than 18%/hour.

Further, since the water-based in the storing state before any recording is performed preferably has an excellent dispersion stability, whereas the water-based ink during the recording is preferably in a state that the pigment easily aggregates, the slope value at the evaporation rate of 0% is preferably smaller than the slope value at the evaporation rate of 30%. Furthermore, the difference obtained by subtracting the slope value at the evaporation rate of 0% from the slope value at the evaporation rate of 30% is, for example, in a range of 0.2 to 10, preferably in a range of 2.0 to 6.0, more preferably in a range of 4.0 to 6.0. By making the difference between the slope value at the evaporation rate of 0% and the slope value at the evaporation rate of 30% to be within the above range, it is possible to further enhance the optical density (OD value) of the water-based ink and to further improve the storing stability of the water-based ink.

The slope values of the water-based ink at the evaporation rates of 0% and 30%, respectively, can be adjusted by, for example, changing the blending amounts of the respective components of the water-based ink. Particularly in a case that the carbon black is used as the pigment, the slope value at the evaporation rate of 0% and the slope value at the evaporation rate of 30% can be easily adjusted in the above ranges, respectively, by allowing the water-based ink to contain the carbon black of which the average particle size of the carbon black is in a range of 140 nm to 160 nm by an amount in a range of 6% by weight to 10% by weight, preferably in a range of 8% by weight to 10% by weight. Further, in a case that the water-based ink contains the glycerol, the slope value at the evaporation rate of 0% and the slope value at the evaporation rate of 30% can be easily adjusted in the above ranges, respectively, also by making the weight ratio (G/P) of the blending amount (G) of the glycerol to the blending amount (P) of the pigment in the water-based ink to be in a range of (G/P)=1.0 to 4.0.

The slope value evaluated by the centrifugal transmission sedimentation method can be obtained, for example, in the following manner. Namely, a dispersion stability analyzer "LUMiFuge" produced by LUM GmbH is used; 0.36 mL of the water-based ink diluted thousand-hold is sealed into a measuring cell of 2 mm×50 mm, and the sealed diluted water-based ink is subjected to centrifugal sedimentation for 2 hours at number of rotation of 3,000 rpm. As the centrifugal sedimentation of the pigment is progressed, the transparency (transmittance) of the water-based ink is increased. During the two hours while the centrifugal sedimentation is performed, the change (increase) in the transmittance of the water-based ink with respect to a light having a wavelength of 865 nm and transmitting through water-based ink is measured and averaged by using a CCD line sensor, and then the slope value (%/hour) as the change in the transmittance per unit time is calculated.

As explained above, in the water-based ink for ink-jet recording of the present teaching, each of the slope value at the evaporation rate of 0% and the slope value at the evaporation rate of 30% is within the predetermined range, and thus the water-based ink for ink-jet recording is capable of realizing both of the high optical density (OD value) and the high storing stability.

Next, an explanation will be given about an ink cartridge of the present teaching. The ink cartridge of the present teaching is characterized by being an ink cartridge containing a water-based ink for ink-jet recording; wherein the water-based ink is the water-based ink for ink-jet recording of the present teaching. For example, any conventionally known main body (body) of an ink cartridge can be used for the main body of the ink cartridge of the present teaching.

Next, explanation will be given about an ink-jet recording apparatus and an ink-jet recording method of the present teaching.

The ink-jet recording apparatus of the present teaching is an ink-jet recording apparatus characterized by including: an ink accommodating section configured to accommodate an ink therein; and an ink discharge mechanism configured to discharge the ink accommodated in the ink accommodating section; wherein the ink accommodated in the ink accommodating section is the water-based ink of the present teaching.

The ink-jet recording method of the present teaching is an ink-jet recording method characterized by including: performing recording on a recording medium by discharging, to the recording medium, a water-based ink by an ink-jet system; and using the water-based ink for ink-jet recording of the present teaching, as the water-based ink.

The ink-jet recording method of the present teaching can be practiced, for example, by using the ink-jet recording apparatus of the present teaching. The recording includes printing a letter (text), printing an image, printing, etc.

FIGURE depicts the configuration of an example of the ink-jet recording apparatus of the present teaching. As depicted in FIGURE, an ink-jet recording apparatus 1 of the present teaching includes four ink cartridges 2, an ink discharge mechanism (ink-jet head) 3, a head unit 4, a carriage 5, a driving unit 6, a platen roller 7 and a purge device 8 as main constitutive components or parts. The ink discharge mechanism (ink-jet head) 3 is preferably an ink-jet head of a piezoelectric system. In particular, with respect to a water-based ink with a high blending amount of the pigment (solid content amount of the pigment), for example, with respect to such a water-based ink in which the content of the pigment is in a range of 6% by weight to 10% by weight, preferably in a range of 8% by weight to 10% by weight, there is such a fear that any burning, etc., might occur when such a water-based ink is discharged by using an ink-jet head of a thermal system. On the other hand, such a water-based ink can be stably discharged by using an ink-jet head of a piezoelectric system.

The four ink cartridges 2 contain four colors of water-based inks, respectively, the four colors being yellow, magenta, cyan and black. At least one water-based ink among the four color water-based inks is the water-based ink for ink-jet recording of the present teaching. The ink-jet head 3 disposed on the head unit 4 performs recording on a recording medium (for example, recording paper or recording sheet) P. The four ink cartridges 2 and the head unit 4 are provided or arranged on the carriage 5. The driving unit 6 reciprocates the carriage 5 in a linear direction. As the driving unit 6, it is possible to use, for example, a conventionally known driving unit (see, for example, Japanese Patent Application laid-open No. 2008-246821 corresponding to United States Patent Application Publication No. US2008/0241398). The platen roller 7 extends in the reciprocating direction of the carriage 5 and is arranged to face or be opposite to the ink-jet head 3.

The purge device 8 sucks or draws unsatisfactory ink (poor ink) which contains air bubbles, etc. accumulated or trapped in the inside of the ink-jet head 3. As the purge device 8, it is possible to use, for example, a conventionally known purge device (for example, see Japanese Patent Application laid-open No. 2008-246821 corresponding to United States Patent Application Publication No. US2008/0241398).

A wiper member 20 is provided on the purge device 8, at a position on the side of the platen roller 7 such that the wiper member 20 is adjacent to the purge device 8. The wiper member 20 is formed to have a spatula shape, and wipes a nozzle-formed surface of the ink-jet head 3 accompanying with the movement (reciprocating movement) of the carriage 5. In FIGURE, a cap 18 is provided to cover a plurality of nozzles of the ink-jet head 3 which is returned to a reset position upon completion of the recording, so as to prevent the water-based inks from drying.

In the ink-jet recording apparatus 1 of the present embodiment, the four ink cartridges 2 are provided, together with the head unit 4, on one carriage 5. However, the present teaching is not limited to this. In the ink-jet recording apparatus 1, the respective four cartridges 2 may be provided on a carriage which is different (separate) from the carriage on which the head unit 4 is provided. Alternatively, the respective four cartridges 2 may be arranged and fixed inside the ink-jet recording apparatus 1, rather than being provided on the carriage 5. In such aspects, for example, each of the four cartridges 2 and the head unit 4 which is provided on the carriage 5 are connected with a tube, etc., and the water-based inks are supplied from the four cartridges 2, respectively, to the head unit 4 via the tubes.

Ink jet recording using the ink-jet recording apparatus 1 is performed, for example, in the following manner. Namely, at first, a recording paper P is supplied or fed, for example, from a paper feeding cassette or sheet feeding cassette (not depicted in the drawing) arranged at a side of or at a position below the ink-jet recording apparatus 1. The recording paper P is introduced or guided between the ink-jet head 3 and the platen roller 7. Then, a predetermined recording is performed on the fed or introduced recording paper P with the water-based ink(s) discharged or jetted from the ink-jet head 3. Since the water-based ink of the present teaching is excellent in the storing stability, the water-based ink can be discharged stably from the ink-jet head 3. The recording paper P after the recording is discharged from the ink-jet recording apparatus 1. According to the water-based ink of the present teaching, it is possible to obtain a recorded matter with a high optical density (OD value). In FIGURE, the paper feeding mechanism and paper discharge mechanism for the recording paper P are omitted in the drawing.

In the apparatus depicted in FIGURE, an ink-jet head of serial type (serial type ink-jet head) is adopted. However, the present teaching is not limited to this. The ink-jet recording apparatus may be an apparatus adopting an ink-jet head of line type (line type ink-jet head).

Next, an explanation will be given about an evaluating method for evaluating water-based ink for ink-jet recording of the present teaching. The evaluating method of the present teaching is a method for evaluating a water-based ink for ink-jet recording containing a pigment such as a carbon black, a surfactant, and water, the method including an evaluation of aggregation of the pigment by the centrifugal transmittance sedimentation method, the evaluation of the aggregation including:

a first evaluation of the aggregation for evaluating a slope value of the water-based ink at an evaporation rate of 0%; and a second evaluation of the aggregation for evaluating a slope value of the water-based ink at an evaporation rate of 30%, wherein dispersion stability of the pigment before recording is evaluated by the first evaluation of the aggregation, and aggregating property of the pigment during the recording is evaluated by the second evaluation of the aggregation.

Conventionally, the dispersion stability and aggregating property of the pigment in the water-based ink are generally evaluated by performing a storing stability evaluating test and a recording test. On the other hand, according to the evaluating method of the present teaching, both of the dispersion stability of the pigment before the recording and the aggregating property of the pigment during the recording can be evaluated by a simple and easy method that is the centrifugal transmission sedimentation method. Namely, according to the evaluating method of the present teaching, a water-based ink in which the slope value is low in the first aggregation evaluation can be judged as a water-based ink in which any discharge failure (unsatisfactory discharge) would not occur due to the aggregation of the pigment. Further, according to the evaluating method of the present teaching, a water-based ink in which the slope value is high in the second aggregation evaluation can be judged as a water-based ink which has a high optical density (OD value). The inventors of the present teaching first found out that the evaluation as to whether or not a water-based ink has a high optical density (OD value) can be performed by the centrifugal transmittance sedimentation method in the manner as described above. In the evaluating method of the present teaching, it is preferable that a water-based ink in which the slope value is not more than 15%/hour in the first aggregation evaluation and in which the slope value is not less than 9%/hour in the second aggregation evaluation is selected as the target water-based ink.

Next, a method for producing the water-based ink for ink-jet recording of the present teaching will be explained. The producing method according to the present teaching is a method for producing a water-based ink for ink-jet recording containing a pigment such as a carbon black, a surfactant, and water, the method including an evaluating step according to the evaluating method for evaluating water-based ink of the present teaching. The other condition(s) of the evaluating method and the producing method of the present teaching are similar to those regarding the water-based ink of the present teaching.

EXAMPLES

Next, examples of the present teaching will be explained together with comparative examples. Note that the present teaching is not limited and is not restricted to the examples and the comparative examples which will be described below.

<Preparation of Carbon Black Water Dispersion A>

40 g of Carbon black "#2650" produced by Mitsubishi Chemical Corporation was mixed to 200 g of ion exchange water, and the obtained mixture was ground or pulverized by a bead mill. A carboxylating agent was then added to the pulverized mixture and heating/stirring operation was performed therefor, followed by an oxidation treatment. Afterwards, the obtained solution (liquid) was cleaned by a solvent a plurality of times, was poured into water, was subjected to a cleaning again with water, and then was subjected to filtration with a filter. Thus, a carbon black water dispersion A was prepared. The average particle size of the carbon black in the carbon black water dispersion A was measured by using a dynamic light scattering particle size distribution measuring apparatus LB-550 manufactured by HORIBA, Ltd.; the average particle size was 156 nm.

Examples 1 to 8 and Comparative Examples 1 to 3

Components, except for the carbon black water dispersion A or a self-dispersible carbon black, which were included in Ink Composition (TABLE 1) as indicated below were mixed uniformly or homogeneously; and thus an ink solvent was obtained. Subsequently, the ink solvent was added to the carbon black water dispersion A or the self-dispersible carbon black dispersed in water, followed by being mixed uniformly. After that, the obtained mixture was filtrated through a cellulose acetate membrane filter (pore size 3.00 μm) produced by Toyo Roshi Kaisha, Ltd., and thus a water-based ink for ink-jet recording of each of Examples 1 to 8 and Comparative Examples 1 to 3 was obtained. Please note that, in TABLE 1, "CAB-O-JET (trade name) 200" is a dispersion of self-dispersible carbon black modified by a sulfonic acid group (sulfonate group), "CAB-O-JET (trade name) 300" is a dispersion of self-dispersible carbon black modified by a carboxyl group.

With respect to the water-based inks of Examples 1 to 8 and Comparative Examples 1 to 3, evaluation of the slope value at the evaporation rate of 0%, evaluation of the slope value at the evaporation rate of 30%, measurement of the optical density (OD value), and evaluation of the storing stability were performed. Note that the evaluations of the slope values at the evaporation rates of 0% and 30%, respectively, the measurement of the optical density (OD value) and the evaluation of the storing stability were performed by the following methods.

<Evaluations of Slope Values at Evaporation Rates of 0% and 30%>

(1) Evaluation of Slope Value at Evaporation Rate of 0%

A dispersion stability analyzer "LUMiFuge" produced by LUM GmbH is used; 0.36 mL of each of the water-based inks of Examples 1-8 and Comparative Examples 1-3 was diluted thousand-hold, was sealed into a measuring cell of 2 mm×50 mm, and the sealed diluted water-based ink of each of Examples 1-8 and Comparative Examples 1-3 was subjected to centrifugal sedimentation for 2 hours at number of rotation of 3,000 rpm. During the two hours while the centrifugal sedimentation was being performed, the change (increase) in the transmittance of the water-based ink with respect to a light having a wavelength of 865 nm and transmitting through water-based ink was measured and averaged by using a CCD line sensor, and then the slope value (%/hour) as the change in the transmittance per unit time was calculated.

(2) Evaluation of Slope Value at Evaporation Rate of 30%

Each of the water-based inks of Examples 1-8 and Comparative Examples 1-3 was heated at 40 degrees Celsius until the weight of the water-based ink was lowered by 30%. The time required for the heating was about 12 hours. The ink after heating of each of Examples 1-8 and Comparative Examples 1-3 was used and the slope value (%/hour) at the evaporation rate of 30% was calculated by a method same as that for obtaining the evaporation rate of 0% as described above.

<Evaluation of Optical Density (OD Value)>

An ink-jet printer "MFC-J4510N" manufactured by BROTHER KOGYO KABUSHIKI KAISHA was used to record an image including a single-color patch on a plain paper, under the conditions with a resolution of 600 dpi×300 dpi, duty: 100% and liquid droplet amount: 35 pL, by using each of the water-based inks of Examples 1 to 8 and Comparative Examples 1 to 3. Thus, evaluation samples were produced. The optical densities (OD values) of each of the evaluation samples at three locations (three portions) of each evaluation sample were measured by using a spectrophotometric colorimetry meter "SpectroEye" (light source: $D_{50}$; field: 2 degrees; density: ANSI T) manufactured by X-Rite Inc., and the average value of the optical densities (OD values) of each of the samples was obtained.

<Evaluation of Storing Stability>

Immediately after preparing the water-based inks of Examples 1 to 8 and Comparative Examples 1 to 3, the viscosity of each of the inks was measured, and each of the water-based inks was stored in a sealed container for two weeks under an environment of 60 degrees Celsius. The viscosity of each of the evaluation samples prepared as described above was measured, and the storing stability of each of the evaluation samples was evaluated based on the following evaluation criterion. The viscosity was measured by using a viscometer (model name: "TVE-25", manufactured by TOKI SANGYO CO., LTD.) under a condition of measurement temperature: 25 degrees Celsius.

<Evaluation Criterion of Storing Stability>

A: There was no increase in the viscosity in the evaluation sample since the time immediately after the preparation of the water-based ink.

B: The rate of increase in the viscosity was less than 3% in the evaluation sample since the time immediately after the preparation of the water-based ink.

C: The rate of increase in the viscosity was not less than 3% in the evaluation sample since the time immediately after the preparation of the water-based ink.

The composition and the results of measurement and evaluation of each of the water-based inks of Examples 1 to 8 and Comparative Examples 1 to 3 are indicated in TABLE 1 as follows.

TABLE 1

| | | | EXAMPLES | | | | | |
|---|---|---|---|---|---|---|---|---|
| | | | 1 | 2 | 3 | 4 | 5 | 6 |
| Composition of water-based ink (% by weight) | Pigment | Carbon Black Water Dispersion A (*1) | 8.00 | — | — | 6.00 | — | — |
| | | CAB-O-JET (trade name) 200 (*2) | — | — | — | — | — | 8.00 |
| | | CAB-O-JET (trade name) 300 (*3) | — | 9.00 | — | — | — | — |
| | | CAB-O-JET (trade name) 400 (*4) | — | — | 8.00 | — | 10.00 | — |
| | | Glycerol | 17.00 | 16.00 | 18.00 | 24.00 | 15.00 | 17.00 |
| | | Dipropylene glycol | — | — | — | — | — | — |
| | | Triethylene glycol | 4.00 | 4.00 | — | 6.00 | — | — |
| | | 2-pyrrolidone | — | — | 2.00 | — | — | 4.00 |
| | | Triethylene glycol-n-butyl ether | 4.00 | 4.00 | — | — | 4.00 | — |
| | | Tripropylene glycol methyl ether | — | — | 4.00 | — | — | 4.00 |
| | | Tripropylene glycol-n-butyl ether | — | — | — | 0.50 | — | — |
| | | NEOPELEX (trade name) G15 (*5) | — | — | — | — | 0.50 | — |
| | | SUNNOL (trade name) NL-1430 (*6) | 0.50 | 0.50 | 0.50 | 0.50 | — | 0.50 |
| | | OLFIN (trade name) E1010 (*7) | — | — | 0.50 | — | — | 0.50 |
| | | OLFIN (trade name) E1004 (*8) | 0.30 | 0.40 | — | 0.50 | 0.40 | — |
| | | Water | balance | balance | balance | balance | balance | balance |
| (G/P): weight ratio (G/P) of the blending amount (G) of the glycerol to the blending amount (P) of the pigment in the water-based ink | | | 2.13 | 1.78 | 2.25 | 4 | 1.5 | 2.13 |
| Slope value at evaporation rate of 0% (%/hour) | | | 12.2 | 5.2 | 6.8 | 8.3 | 8.7 | 5.8 |
| Slope value at evaporation rate of 30% (%/hour) | | | 16.1 | 9.00 | 11.7 | 12.2 | 12.4 | 9.5 |
| Optical Density (OD value) | | | 1.37 | 1.27 | 1.27 | 1.27 | 1.29 | 1.25 |
| Storing Stability | | | A | B | B | A | B | B |

| | | | EXAMPLES | | COMPARATIVE EXAMPLES | | |
|---|---|---|---|---|---|---|---|
| | | | 7 | 8 | 1 | 2 | 3 |
| Composition of water-based ink (% by weight) | Pigment | Carbon Black Water Dispersion A (*1) | 8.00 | 8.00 | 4.00 | — | 11.00 |
| | | CAB-O-JET (trade name) 200 (*2) | — | — | — | — | — |
| | | CAB-O-JET (trade name) 300 (*3) | — | — | — | 6.00 | — |
| | | CAB-O-JET (trade name) 400 (*4) | — | — | — | — | — |
| | | Glycerol | 20.00 | 17.00 | 30.00 | 12.00 | 10.00 |

TABLE 1-continued

|  | | | | | |
|---|---|---|---|---|---|
| Dipropylene glycol | 2.00 | — | — | — | — |
| Triethylene glycol | — | 4.00 | 4.00 | — | 5.00 |
| 2-pyrrolidone | — | — | — | 3.00 | — |
| Triethylene glycol-n-butyl ether | 4.00 | — | 4.00 | — | — |
| Tripropylene glycol methyl ether | — | 4.00 | — | 2.00 | — |
| Tripropylene glycol-n-butyl ether | — | — | — | — | 1.00 |
| NEOPELEX (trade name) G15 (*5) | 0.50 | — | — | — | — |
| SUNNOL (trade name) NL-1430 (*6) | — | 1.50 | 0.50 | 0.50 | 0.50 |
| OLFIN (trade name) E1010 (*7) | — | — | — | — | — |
| OLFIN (trade name) E1004 (*8) | 0.10 | 0.60 | 0.40 | 0.40 | 0.40 |
| Water | balance | balance | balance | balance | balance |
| (G/P): weight ratio (G/P) of the blending amount (G) of the glycerol to the blending amount (P) of the pigment in the water-based ink | 2.5 | 2.13 | 7.5 | 2 | 0.91 |
| Slope value at evaporation rate of 0% (%/hour) | 11.8 | 11.8 | 6.1 | 3.3 | 15.2 |
| Slope value at evaporation rate of 30% (%/hour) | 16.0 | 16.0 | 8.4 | 5.1 | 21.9 |
| Optical Density (OD value) | 1.23 | 1.38 | 1.15 | 1.19 | 1.45 |
| Storing Stability | A | B | A | A | C |

LEGEND
(*1) Average particle size: 156 nm; numerals in the table indicate solid content blending amount.
(*2) Self-dispersible carbon black; produced by Cabot Specialty Chemicals, Inc.; average particle size: 130 nm; numerals in the table indicate solid content blending amount.
(*3) Self-dispersible carbon black; produced by Cabot Specialty Chemicals, Inc.; average particle size: 123 nm; numerals in the table indicate solid content blending amount.
(*4) Self-dispersible carbon black; produced by Cabot Specialty Chemicals, Inc.; average particle size: 130 nm; numerals in the table indicate solid content blending amount.
(*5) Anionic surfactant; produced by Kao Corporation; active ingredient amount = 16% by weight.
(*6) Anionic surfactant; produced by Lion Corporation; active ingredient amount = 28% by weight.
(*7) Nonionic surfactant; produced by Nisshin Chemical Co., Ltd.; active ingredient amount = 100% by weight.
(*8) Nonionic surfactant; produced by Nisshin Chemical Co., Ltd.; active ingredient amount = 100% by weight.

As indicated in TABLE 1, Examples 1 to 8 were capable of realizing both of the high optical density (OD value) and the high storing stability. In Examples 1, 4 and 7 in each of which the average particle size of the carbon black was in a range of 140 nm to 160 nm and the nonionic surfactant ratio was in a range of 0.1% by weight to 0.5% by weight, the result of evaluation of the storing stability was particularly excellent. Further, in Examples 1 and 4 in each of which the average particle size of the carbon black was in the range of 140 nm to 160 nm and the nonionic surfactant ratio was in a range of 0.2% by weight to 0.5% by weight, the optical density (OD value) was not less than 1.27 and was particularly high. Further, in each of Examples 1 to 8, the blending amount of the pigment was in a range of 6% by weight to 10% by weight, and the weight ratio (G/P) of the blending amount (G) of the glycerol to the blending amount (P) of the pigment in the water-based ink was in a range of (G/P)=1.0 to 4.0.

Furthermore, the inks of Examples 1, 7 and 8 used a carbon black of which average particle size was in the range of 140 nm to 160 nm by a same blending amount; and the rate of the nonionic surfactant were 0.30% by weight, 0.10% by weight and 0.60% by weight, respectively. When comparing Examples 1, 7 and 8, the slope value at the evaporation rate 30% was substantially same among the inks of Examples 1, 7 and 8. However, as the ratio of the nonionic surfactant was higher, the optical density (OD value) was increased to be higher. A high optical density (OD value) could be obtained in a case that the slope value at the evaporation rate of 30% was not less than 9%/hour. It was appreciated, however, that the optical density (OD value) could be increased to be higher by adding, to the water-based ink, the nonionic surfactant having the characteristic of spreading laterally on the recording medium. Moreover, among Examples 1, 7 and 8, Example 7 in which the ratio of the nonionic surfactant was less than 0.2% by weight (0.10% by weight) had a low optical density (OD value) (1.23), as compared with Examples 1 and 8; and Example 8 in which the ratio of the nonionic surfactant was more than 0.5% by weight (0.60% by weight) had an unsatisfactory result in the evaluation of storing stability (result of evaluation: B). Since the nonionic surfactant has a low solubility to water, it is presumed that if the blending amount of the nonionic surfactant is increased, the storing stability is adversely affected. From the comparison among Examples 1, 7 and 8, it is appreciated that the optical density (OD value) and the storing stability can be enhanced further at the same time by making the ratio of the nonionic surfactant to be within the range of 0.2% by weight to 0.5% by weight.

On the other hand, in Comparative Examples 1 and 2 in each of which the slope value at the evaporation rate of 30% was less than 9%/hour, the optical density (OD value) was low (1.15 and 1.19, respectively), and in Comparative Example 3 in which the slope value at the evaporation rate of 0% exceeded 15%/hour, the result of evaluation of the storing stability was unsatisfactory (result of evaluation: C). Comparative Examples 1 and 3 each used the carbon black of which average particle size was in the range of 140 nm to 160 nm, and the blending amounts of the carbon black were 4.0% by weight and 11% by weight, respectively. In Comparative Example 1, since the blending amount of the pigment was less than 6% by weight, it is presumed that even the ink at the evaporation rate of 30% hardly aggregated, and thus the ink of Comparative Example 1 had a low optical density (OD value) (1.15). Namely, in Comparative Example 1, the small blending amount of the pigment is presumed as a factor for resulting in the slope value at the evaporation rate of 30% that was less than 9%/hour. On the other hand, in Comparative Example 3, since the blending amount of the pigment was more than 10% by weight (11.00% by weight), it is presumed that even the ink at the evaporation rate of 0% easily aggregated, and thus the ink of Comparative Example 3 was evaluated to have a lowest result in the evaluation of storing stability (result of evaluation: C). Namely, in Comparative Example 3, the large blending amount of the pigment is presumed as a factor for resulting in the slope value at the evaporation rate of 0% that exceeded 15%/hour (15.2%/hour). From the results of Comparative Examples 1 and 3, in order to realize both of the high optical density (OD value) and the high storing stability, it is presumed that the water-based ink contains the carbon black, of which average particle size is in the range of 140 nm to 160 nm, preferably by the amount in the range of 6% by weight to 10% by weight, more preferably in the range of 8% by weight to 10% by weight.

Further, in Comparative Example 1, the weight ratio (G/P) of the blending amount (G) of the glycerol to the blending amount (P) of the pigment in the water-based ink was (G/P)=30/4=7.5, namely, exceeded 4.0. Accordingly, in Comparative Example 1, it is presumed that even in the ink at the evaporation rate of 30%, the pigment was satisfactorily dispersed and thus hardly aggregated, and thus the ink of Comparative Example 1 had a low optical density (OD value) (1.15). Namely, in Comparative Example 1, a large weight ratio (G/P) is also presumed to be a factor for resulting in the slope value at the evaporation rate of 30% that was less than 9%/hour (8.4%/hour). On the other hand, in Comparative Example 3, the weight ratio (G/P) was (G/P)=10/11=0.91, namely, less than 1.0. Accordingly, in Comparative Example 3, it is presumed that even in the ink at the evaporation rate of 0%, the pigment was unsatisfactorily dispersed, and thus the ink of Comparative Example 3 was evaluated to have a lowest result in the evaluation of storing stability (result of evaluation: C). Namely, in Comparative Example 3, a small weight ratio (G/P) is also presumed to be a factor for resulting in the slope value at the evaporation rate of 0% that exceeded 15%/hour (15.2%/hour). From the comparison between Comparative Examples 1 and 3, it is appreciated that in order to realize both of the high optical density (OD value) and the high storing stability, it is presumed that the weight ratio (G/P) of the blending amount (G) of the glycerol to the blending amount (P) of the pigment in the water-based is preferably made to be within the range of 1.0 to 4.0.

In Comparative Example 2, although the blending amount of the carbon black was 6% by weight, the average particle size of the carbon black was less than 140 nm. Since the average particle size of the carbon black was small in Comparative Example 2, it is presumed that even in the ink at the evaporation rate of 30%, the pigment was satisfactorily dispersed and thus hardly aggregated, and thus the ink of Comparative Example 2 had a low optical density (OD value) (1.19). Namely, in Comparative Example 2, a small average particle size of the carbon black is presumed to be a factor for resulting in the slope value at the evaporation rate of 30% that was less than 9%/hour (5.1%/hour). On the other hand, although Example 4 used, as the pigment, the carbon black water dispersion A different from that used in Comparative Example 2, the kind of the pigment used in Example 4 was a self-dispersible carbon black modified by the carboxylic acid group that was similar to that used in Comparative Example 2, and the blending amount of the pigment was 6% by weight in Example 4. Note that, however, the average particle size of the carbon black used in Example 4 was in the range of 140 nm to 160 nm (156 nm) which was greater than that in Comparative Example 2. Namely, in Example 4, a large average particle size of the carbon black is presumed to be a factor for resulting in the slope value at the evaporation rate of 30% that was not less than 9%/hour (12.2%/hour) and in the satisfactory aggregation of the ink at the evaporation rate of 30%.

As described above, the water-based ink of the present teaching is capable of realizing both of the high optical density (OD value) and the high storing stability. The usage of the water-based ink of the present teaching is not particularly limited, and is widely applicable to a variety of kinds of ink-jet recording.

What is claimed is:

1. A water-based ink for ink-jet recording comprising:
   a pigment;
   a surfactant; and water,
   wherein a slope value of the water-based ink at an evaporation rate of 0% is not more than 15%/hour;
   a slope value of the water-based ink at an evaporation rate of 30% is not less than 9%/hour,
   the slope value of the water-based ink being measured by a centrifugal transmission sedimentation method;
   the surfactant is a nonionic surfactant and a content of the surfactant in the water-based ink is in a range of 0.2% by weight to 0.5% by weight; and
   the pigment is a carbon black of which an average particle size is in a range of 140 nm to 160 nm and a content of the carbon black in the water-based ink is in a range of 8% by weight to 10% by weight.

2. The water-based ink for ink-jet recording according to claim 1, wherein the pigment is a self-dispersible carbon black.

3. The water-based ink for ink-jet recording according to claim 1, wherein the pigment is a self-dispersible carbon black modified by a carboxyl group.

4. The water-based ink for ink-jet recording according to claim 1, wherein the surfactant is an acetylenic glycol-based nonionic surfactant represented by the following formula (1):

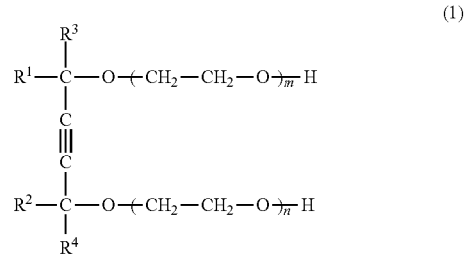

in the formula (1), "m" and "n" are identical to each other or different from each other, and are numbers satisfying: m+n=1 to 15; and
$R^1$, $R^2$, $R^3$ and $R^4$ are identical to one another or different from one another, and each of $R^1$, $R^2$, $R^3$ and $R^4$ is a straight-chain or branched-chain alkyl group of which carbon atom number is 1 to 5.

5. The water-based ink for ink-jet recording according to claim 4, wherein in the formula (1), the "m" and "n" are numbers satisfying: m+n=1 to 6.

6. The water-based ink for ink-jet recording according to claim 4, wherein the surfactant contains the acetylenic glycol-based nonionic surfactant represented by the formula (1) and an anionic surfactant; and
a weight ratio (A/N) of a blending amount (A) of the anionic surfactant to a blending amount (N) of the acetylenic glycol-based nonionic surfactant represented by the formula (1) in the water-based ink is in a range of 0.2 to 0.8.

7. The water-based ink for ink-jet recording according to claim 4, wherein a weight ratio (N/P) of a blending amount (N) of the acetylenic glycol-based nonionic surfactant represented by the formula (1) to a blending amount (P) of the pigment in the water-based ink is in a range of 1.2/100 to 8.4/100.

8. The water-based ink for ink-jet recording according to claim 4, wherein HLB of the acetylenic glycol-based nonionic surfactant represented by the formula (1) is in a range of 8 to 12.

9. The water-based ink for ink-jet recording according to claim 1, further comprising glycerol, and a content of the glycerol in the water-based ink is in a range of 15% by weight to 25% by weight.

10. The water-based ink for ink-jet recording according to claim 1, further comprising glycerol;
   wherein a weight ratio (G/P) of a blending amount (G) of the glycerol to a blending amount (P) of the pigment in the water-based ink is in a range of 1.0 to 4.0.

11. The water-based ink for ink-jet recording according to claim 1, wherein the slope value of the water-based ink at the evaporation rate of 0% is in a range of 5%/hour to 15%/hour; and
   the slope value of the water-based ink at the evaporation rate of 30% is in a range of 9%/hour to 18%/hour.

12. A method for evaluating a water-based ink for ink-jet recording containing a pigment, a surfactant and water, the method comprising:
   performing a first evaluation of aggregation for measuring a slope value of the water-based ink at an evaporation rate of 0%, by a centrifugal transmittance sedimentation method; and
   performing a second evaluation of aggregation for measuring a slope value of the water-based ink at an evaporation rate of 30%, by the centrifugal transmittance sedimentation method.

13. The method for evaluating the water-based ink for ink-jet recording according to claim 12, wherein dispersion stability of the pigment before recording is evaluated by the first evaluation of the aggregation; and
   aggregating property of the pigment during the recording is evaluated by the second evaluation of the aggregation.

* * * * *

UNITED STATES PATENT AND TRADEMARK OFFICE
CERTIFICATE OF CORRECTION

PATENT NO. : 9,718,977 B2
APPLICATION NO. : 14/867651
DATED : August 1, 2017
INVENTOR(S) : Yuka Tsuzaka et al.

It is certified that error appears in the above-identified patent and that said Letters Patent is hereby corrected as shown below:

On the Title Page

Under Abstract, Item (57), Line 1:
Please delete "ink jet-recording" and insert --ink-jet recording--

Signed and Sealed this
Twentieth Day of February, 2018

Andrei Iancu
*Director of the United States Patent and Trademark Office*